United States Patent [19]
Esanu

[11] 3,984,414
[45] Oct. 5, 1976

[54] DICHLOROACETATE SALT OF 2-ISOPROPYLAMINO PYRIMIDINE

[75] Inventor: Andre Esanu, Paris, France

[73] Assignee: Societe d'Etudes de Produits Chimiques, Issy-les-Moulineaux, France

[22] Filed: Nov. 19, 1974

[21] Appl. No.: 525,101

Related U.S. Application Data

[63] Continuation of Ser. No. 287,503, Sept. 8, 1972, abandoned.

[30] Foreign Application Priority Data

Oct. 9, 1971 United Kingdom............ 47130/71

[52] U.S. Cl........................... 260/256.4 N; 424/251
[51] Int. Cl.²....................................... C07D 239/42
[58] Field of Search............................ 260/256.4 N

[56] References Cited

UNITED STATES PATENTS 2,455,172    11/1948    Hearne et al. ..................... 260/251

OTHER PUBLICATIONS

Esanu, "Chemical Abstracts," vol. 79, 1973, Col. 96981a, (Abstract of Belgium Pat. No. 788,648, patented 1/2/73).

*Primary Examiner*—Alton D. Rollins
*Assistant Examiner*—James H. Turnipseed
*Attorney, Agent, or Firm*—Eyre, Mann, Lucas & Just

[57] ABSTRACT

Dichloro acetate of 2-isopropyl amino pyrimidine is an active ingredient in drug for the treatment of neuropathies.

1 Claim, No Drawings

THE DICHLOROACETATE SALT OF 2-ISOPROPYLAMINO PYRIMIDINE

This is a continuation of application Ser. No. 287,503, filed Sept. 8, 1972, now abandoned.

This invention relates to a salt of a 2-substituted amino pyrimidine derivative. The new pyrimidine derivative salt provided by this invention is useful as an active agent in medicines for the treatment of neuropathies.

This invention provides the dichloro acetate of 2-isopropyl amino pyrimidine, which has the formula:

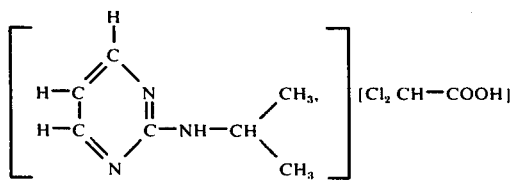

It is a white crystalline powder with a bitter flavour, which melts at 55°C, and is soluble in water, ethanol and chloroform. Its formula is $C_9H_{13}O_2N_3Cl_2$ and its molecular weight is 2.66 l.

This compound may be obtained by reacting 2-isopropyl amino pyrimidine with dichloro acetic acid, suitably in a solvent, for example, a lower alkyl hydrocarbon.

This invention is illustrated by the following example:

EXAMPLE 0.1 liter of pentane and 27.4 g (0.2 mole) of 2-isopropylamino pyrimidine were added to a 2-liter flask and stirred. The solution was then cooled and there was slowly added a solution of 25.8 g (0.2 mole) of dichloracetic acid in 0.1 liter of pentane. The stirring was maintained for one hour and the resulting precipitate was filtered and washed with isopentane. The product was recrystallized from isopropryl oxide. Yield : 83 %.

On analysis the compound was found to correspond to the formula $C_9H_{13}O_2N_3Cl_2$ as can be seen from the comparison of the actual and theoretical results of elemental analysis:

|        | C     | H    | O     | N     | Cl    |
|--------|-------|------|-------|-------|-------|
| Found  | 40.66 | 4.71 | 11.87 | 15.66 | 27.00 |
| Theory | 40.62 | 4.92 | 12.02 | 15.79 | 26.64 |

TOXICITY

Toxicity has been studied on mice by the usual techniques; LD 50 is 1g/kg intraperitoneously and 3 g/kg per os.

PHARMACOLOGY

The pharmacological activity has been established by three methods.

1. Regeneration of Nervous Fibres

This regeneration was determined by Tangari's method (described in "Ricerche Sperimentali sull l'azione dell aneuria nei processi rigeneration del tissuto nervosi peripherico". Arch. Sci. Med. 69 334/345, 1940). The sciatic nerve of a rat is crushed which results in the degeneration of the motory and sensitive fibres. Regeneration is measured by the reappearance of reaction at excitation and heat (sensitive fibres) or by the reappearance of spontaneous motion of the leg (motory fibres).

Doses were 50 mg/kg intraperitoneously. The results are reported in the following tables with comparative values obtained simultaneously with vitamins $B_1$, $B_6$ and $B_{12}$ and with controls.

|  | Reappearance of Sensitiveness | | | Reappearance of motivity | | |
|---|---|---|---|---|---|---|
|  | 15 days after crushing | 22 days after crushing | 29 days after crushing | 15 days after crushing | 22 days after crushing | 29 days after crushing |
| Standard $B_1$ 500μg/kg + $B_6$ 500μg/kg I.P. + $B_{12}$ 5μg/kg | 0 % | 87 % | 100 % | 0 % | 80 % | 95 % |
| dichloro acetate of 2-isopropyl amino pyrimidine I.P. | 20 % | 100 % | 100 % | 0 % | 87 % | 100 % |
| Controls | 0 % | 30 % | 100 % | 0 % | 0 % | 100 % |

2. Protection against painful syndrom at phenylquinone. This is the Siegmund's test (described in "A method for evaluation both non-narcotic and narcotic analgesies". Proc. Soc. Exp. Biol. Med. 1957, 95, pp. 729/31 — SIEGMUND E. A., CADMUS R. A., GO LU). The ED 50 is 20 mg/kg intraperitoneously and 140 mg/kg per os (on mice).

3. Cardiovascular Study

A good peripheral vasodilatation (femoral) can be noticed on dogs receiving intravenously 4 mg/kg.

PRESENTATION — POSOLOGY

This salt can be presented in any therapeutically acceptable form and, for instance, in gelatine capsules containing 50 mg per dosage unit together with an excipient such as lactose; for injectable form the product may be dosed in phials containing at least 10 mg of active ingredient dissolved in water.

I claim:
1. Dichloro acetate of 2-isopropyl amino pyrimidine.

* * * * *